(12) United States Patent
Prabhu et al.

(10) Patent No.: US 10,646,343 B2
(45) Date of Patent: May 12, 2020

(54) SYSTEM AND METHOD FOR VALVE ACTIVATION

(71) Applicant: Abbott Cardiovascular Systems Inc., Santa Clara, CA (US)

(72) Inventors: Santosh Prabhu, Sunnyvale, CA (US); Jacob L. Greenberg, Redwood City, CA (US); Koji J. Kizuka, San Francisco, CA (US); Travis Marsot, Mountain View, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 182 days.

(21) Appl. No.: 15/796,629

(22) Filed: Oct. 27, 2017

(65) Prior Publication Data

US 2019/0125536 A1 May 2, 2019

(51) Int. Cl.
*A61F 2/24* (2006.01)
*A61N 2/02* (2006.01)
*A61N 2/00* (2006.01)
*A61F 2/30* (2006.01)

(52) U.S. Cl.
CPC .......... *A61F 2/2478* (2013.01); *A61F 2/2463* (2013.01); *A61N 2/004* (2013.01); *A61N 2/02* (2013.01); *A61F 2002/30291* (2013.01); *A61F 2210/009* (2013.01); *A61F 2230/0052* (2013.01); *A61F 2250/0001* (2013.01); *A61F 2250/0014* (2013.01); *A61F 2250/0029* (2013.01)

(58) Field of Classification Search
CPC ........ A61F 2/2463; A61F 2/2478; A61N 2/02
USPC .......................................................... 600/16
See application file for complete search history.

(56) References Cited

U.S. PATENT DOCUMENTS

| | | |
|---|---|---|
| 4,979,955 A | 12/1990 | Smith |
| 2007/0027460 A1 | 2/2007 | Case et al. |
| 2012/0245678 A1* | 9/2012 | Solem ................. A61M 1/1081 623/2.36 |

* cited by examiner

*Primary Examiner* — Joseph M Dietrich
(74) *Attorney, Agent, or Firm* — Baker Botts L.L.P.

(57) ABSTRACT

A method for improving the function of a valve in the heart of a patient, comprising attaching, to a leaflet of the valve, an element that is responsive to a magnetic field; positioning, outside of the heart of the patient, a coil connected to a source of electric energy; activating the source of electric energy to provide an oscillating current in the coil; and thereby providing an oscillating magnetic field through the coil to effect movement of the element and the leaflet.

14 Claims, 7 Drawing Sheets

SYSTEM AND METHOD FOR VALVE ACTIVATION

The present invention relates to systems and methods for correcting deficiencies that may arise in the operation of the human heart, specifically in the operation of valves in the human heart.

Figure 1:
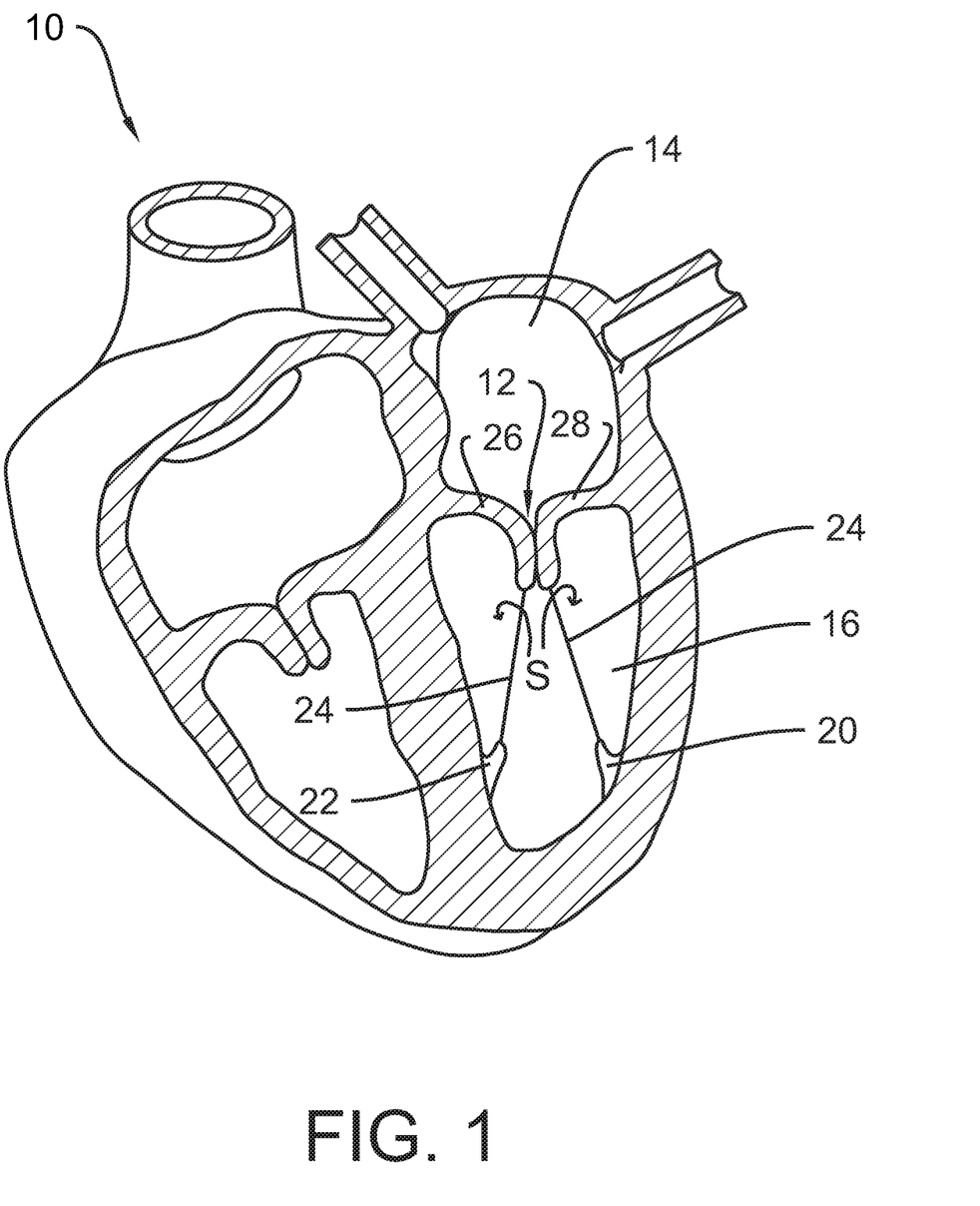
FIG. 1 shows a sectional view of the heart of a human subject in which the leaflets in the mitral valve coapt properly during systole, and blood cannot escape from the left ventricle into the left atrium.
Figure 2:
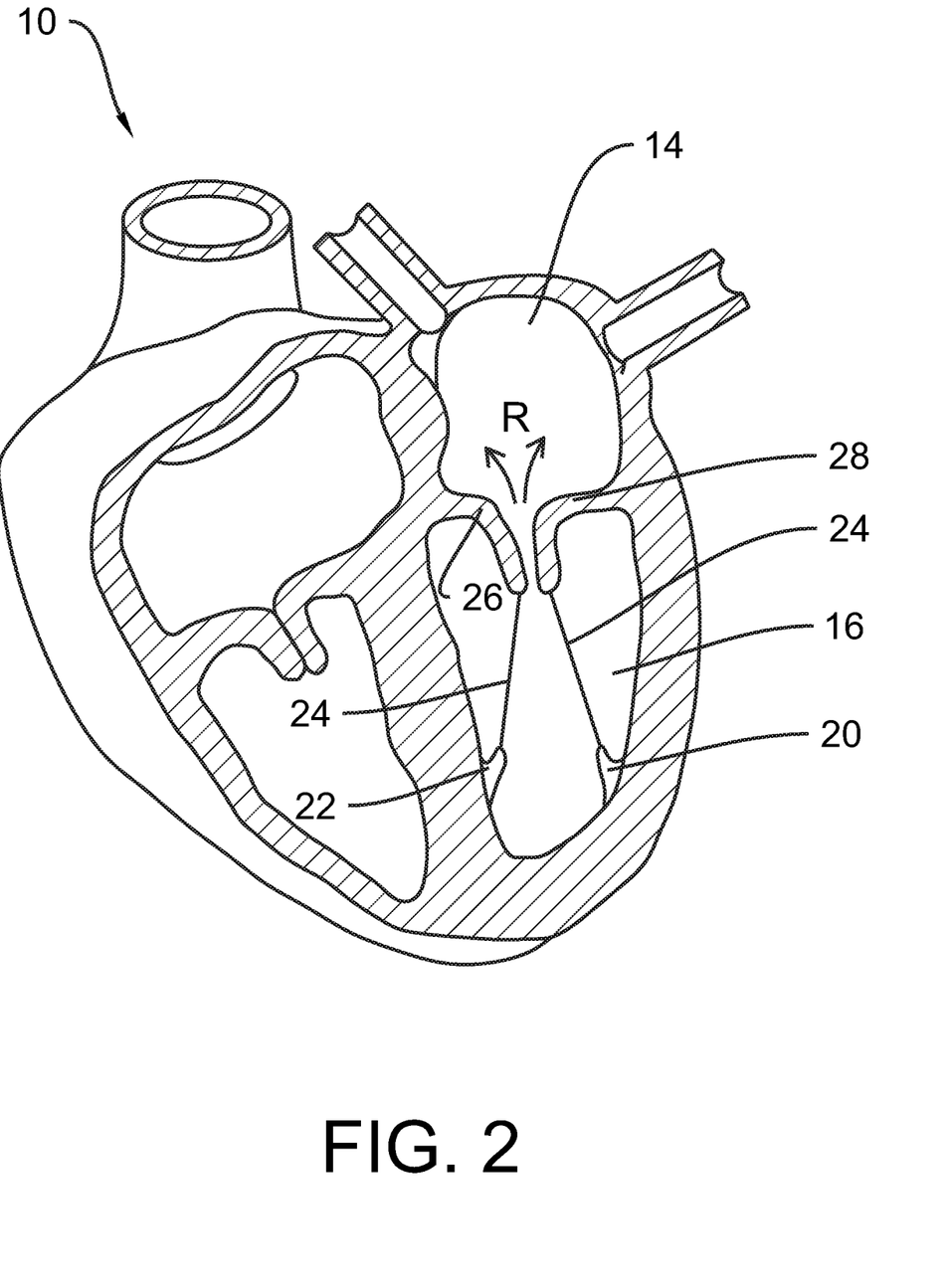
FIG. 2 shows the sectional view of FIG. 1, in which the leaflets in the mitral valve fail to coapt during systole, and blood escapes (arrows R) from the left ventricle into the left atrium.

An understanding of the human heart, and of deficiencies that may arise in the human heart, may be better understood with reference to the accompanying drawings, FIG. 1 and FIG. 2.

FIG. 1 shows a sectional view of the heart 10 of a human subject. The mitral valve 12 is located between the left atrium 14 and left ventricle 16, generally adjacent to the aortic valve (not shown). The papillary muscles 20, 22 are finger-like muscular projections that extend from the wall of the left ventricle, as shown. Inelastic tendons, known as the chordae tendineae 24 extend from the antero-lateral papillary muscle 20 and from the postero-medial papillary muscle 22 to the anterior leaflet 26 and posterior leaflet 28 of the mitral valve 12, as shown. When connected at this level in relation to the rest of the heart, the papillary muscle(s) serve, in part, to limit movement of the mitral and tricuspid valve leaflets. During the diastolic phase of the cardiac cycle, the left ventricular myocardium relaxes, thus causing the pressure within the left ventricle to decrease and causing the mitral valve leaflets to open as blood travels from the left atrium into the left ventricle. Thereafter, during the systolic phase of the cardiac cycle, the left ventricle contracts, thereby causing an increase in pressure within the left ventricle. This increase in left ventricular pressure causes the mitral valve leaflets 26, 28 to coapt and close, preventing the escape of blood into the atrium, as schematically shown by the arrows S in FIG. 1.

Mitral valve regurgitation (also known as mitral insufficiency or mitral incompetence) results when the leaflets 26, 28 of the mitral valve do not fully coapt (i.e., do not close tightly), thus allowing blood to backflow from the left ventricle 16 into the left atrium during the systolic phase of the cardiac cycle—as schematically shown by the arrows R in FIG. 2. This can result in decreased cardiac output and inadequate perfusion of tissues throughout the body, with various resultant symptoms, including severe fatigue and shortness of breath. Although the foregoing problems are identified in relation to the mitral valve, the same problems arise also in the tricuspid valve. Accordingly, solutions are sought with respect to both valve types in the heart.

Some methods of correction have been developed that utilize the effect of pairs of magnets attached to the leaflets of a defective valve, or to prosthetic valves that have been specifically developed and implanted into the heart of a patient. For example, some systems have been developed that rely on one magnet on each of the original leaflets 26, 28 of a valve, where the magnets have opposite polarity. However, this system introduces problems in that the strength of the magnets is inherently non-linear, and may be too strong when they are close to each other, but too weak when spaced apart. Thus, a set of magnets may become permanently attached to each other, with the result of blocking the blood flow. Further systems have sought to temporarily introduce an electromagnet into the heart to operate two non-magnet (but magnet field permeable) elements on each of the leaflets. Other systems have developed a prosthetic valve, in which a valve leaf is operated by activating an electromagnet which is part of the prosthetic structure inside the heart. However, such latter systems are complicated by the fact that they require open heart surgery for implantation, and are additionally complicated by the need to power an electrically operated system inside the heart.

Therefore, devices, systems and methods are desired which may solve the needs of the prior art. The present invention addresses these and other needs.

SUMMARY OF THE INVENTION

In one embodiment, the invention is a method for improving the function of a valve in the heart of a patient. The valve may be either a mitral valve, or a tricuspid valve. The method comprises the steps of attaching, to a leaflet of the valve, an element that is responsive to a magnetic field. Then in an additional step, a coil is connected to a source of electric energy and is positioned outside of the heart of the patient. When these steps are performed, the source of electric energy is activated to provide an oscillating current in the coil. These actions provide an oscillating magnetic field through the coil to effect movement of the element and the leaflet.

In some embodiments, attaching an element to a leaflet of the valve includes attaching an element by transcatheter procedure. In further embodiments, attaching an element to a leaflet of the valve includes attaching an element that includes a rare earth metal. In yet further embodiments, attaching an element to a leaflet of a valve includes shortening a free edge of the leaflet.

In some embodiments, attaching an element comprises positioning, above a leaflet of the valve, a first cylinder, and further, positioning, below the leaflet, a clip having an axial length and comprising a second cylinder having a wall and an internal bore, wherein the wall defines an opening extending along the axial length. (The terms "above" and "below" with reference to a leaflet may, as used in this application, be interpreted to include the reverse orientation because the principle of the invention is applicable without limitation to vertical orientation of the steps and structures in relation to the leaflet.) Then, the first cylinder is pressed radially toward the second cylinder and through the opening into the internal bore, and simultaneously a portion of the leaflet is forced into the internal bore between the first cylinder and the second cylinder. Under this process, pressing the first cylinder through the opening into the internal bore may include elastically bending the second cylinder to temporarily widen the opening. In some embodiments, positioning a first cylinder and positioning a clip may be performed using a transcatheter procedure. A further step may include positioning an elongate element to extend along a free edge of the leaflet. This elongate element may be connected to the clip, so that the two features work in unison.

In some embodiments, positioning, outside of the heart of the patient, a coil connected to a source of electric energy may include implanting a coil inside a torso of the patient. Under this arrangement, implanting a coil may include implanting a coil between a wall of the heart and a left lung. In further embodiments, implanting a coil may include implanting a source of electric energy inside a torso of the patient. Under this arrangement, a further step may include recharging the source of electric energy from a second source of electric energy located outside the torso by a process of electromagnetic induction.

In yet further embodiments, providing an oscillating magnetic field may include measuring a first frequency of a heart rate of the patient and then synchronizing a second frequency of the oscillating magnetic field with the first frequency. Under this arrangement, synchronizing the second frequency with the first frequency may include forcing the leaflet into coaptation with an opposing leaflet during a systole of the heart, and forcing the leaflet out of coaptation during a diastole of the heart.

These and other advantages of the invention will appear when read in conjunction with the figures, and the detailed description of some embodiments.

DETAILED DESCRIPTION OF THE PREFERRED EMBODIMENTS

With reference to the figures, a description is provided of some embodiments having features of the invention. As used herein, the term "transcatheter" is used to describe a minimally invasive technique to enter the heart using a catheter via body lumens that give access to the heart, and may include penetrating a wall such as a septum with the catheter in a trans septal variation of the transcatheter procedure.

FIG. 1 and FIG. 2 have been described above. FIG. 1 shows a healthy heart valve in which coaptation of valve leaflets 26, 28 is achieved, and FIG. 2 shows an unhealthy heart valve in which leaflet coaption is not achieved so that regurgitation takes place as schematically indicated by arrows R.

Figure 3:
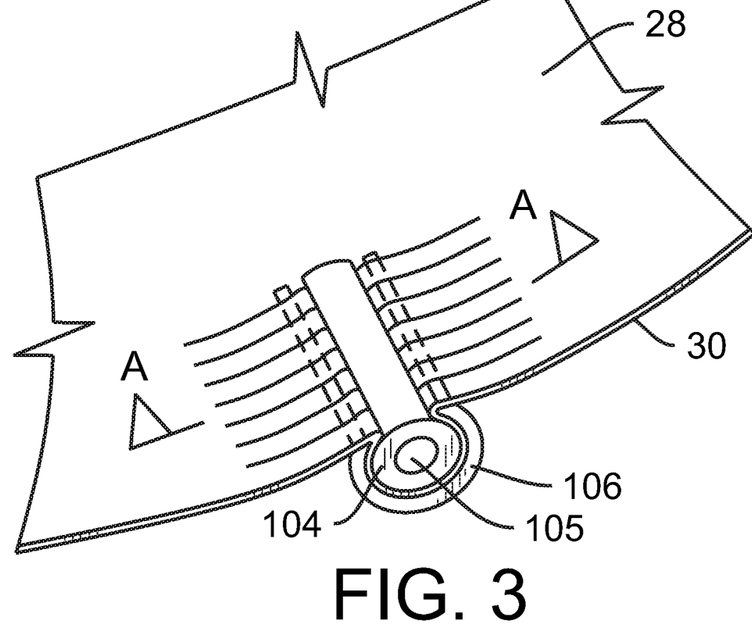
FIG. 3 shows a schematic perspective view of a valve leaflet of a human heart onto which a system with magnetic properties has been attached.

FIG. 3 shows an example of a system and method that accomplishes two objectives simultaneously. The first objective is to shorten the length of the free edge 30 of a leaflet 28 that fails to coapt with an opposing leaflet. The first objective is the subject of an application which is owned by the present applicant, under application Ser. No. 15/445,789, and which is incorporated herein by reference in its entirety. There are other known systems for accomplishing this first objective. For example application Ser. No. 14/761,683 (published as U.S. Publication 2016/0038149) accomplishes a similar result, also by using a transcatheter technique. Both are capable of shortening the length of the free edge of a leaflet of a valve.

The second objective is addressed in the instant application, and is described in detail herein. The second objective may be accomplished to include any of the described methods for shortening the length of the free edge of a leaflet in some embodiments. However, other methods may be used that do not shorten the length of the free edge of the leaflet in further embodiments. The second objective is to use one of the described methods of the first objective in order to attach a structure with magnetic properties to a leaflet, so that it may participate in a system for activating and moving the leaflet at the same frequency as the heartbeat of the patient, as will be described herein.

The method and structure that is exemplified in FIG. 3 comprises attaching, for example, two separate elements to the leaflet 28 with the effect of taking up slack in the free edge 30 of the leaflet. This is the method described in application Ser. No. 15/445,789. Thus, in some embodiments, the structure for attachment to a leaflet may consist of only a hollow cylinder 104 defining an internal bore 105, and a clip 106 comprising an internal bore 107. As understood with reference to FIG. 4, a sectional view of the system in a condition where it is applied to the leaflet, the clip 106 has an internal bore 107 which is shown to have an internal diameter D1 that is larger than the external diameter D2 of the cylinder 104. D1 is sufficiently large to receive both the cylinder and also the leaflet 28 which may be wrapped around the cylinder 104 as described here below. Furthermore, the clip 106 may be envisaged as a hollow cylinder from which a portion D3 of its cylindrical wall has been removed. The size of the opening D3 in the cylindrical wall from which the portion has been removed is preferably smaller than the diameter D2 of the cylinder 104. However, the clip 106 is configured to permit the cylinder to be squeezed into the opening D3, such that the clip bends slightly under elastic deformation to permit entry of the cylinder, and then to snap back so as to hold the cylinder 104 (surrounded by leaflet 28) inside the clip 106. Thus, D1 is sufficiently small to prevent the cylinder 104 from falling out of the bore, once the first cylinder has been received into the bore of the second cylinder.

Figure 4:
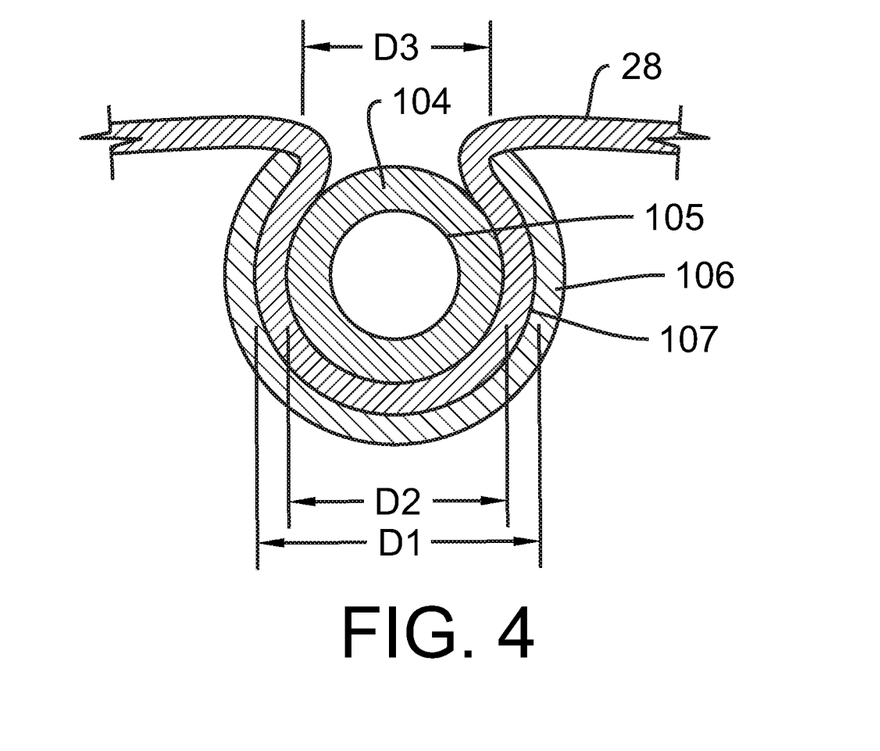
FIG. 4. is a sectional view of the valve leaflet in FIG. 3, taken substantially along the line A-A in FIG. 3.

Following a transcatheter method of delivery that is described in application Ser. No. 15/445,789, the cylinder 104 is positioned above the leaflet 28, and the clip 106 is positioned below the leaflet. The cylinder 104 and clip 106 are then, from this starting position, gently forced towards each other while the leaflet 28 is positioned between them. The cylinder is gently forced through the opening D3 of the clip 106. At a certain point, the clip surrounds the cylinder, and snaps closed to capture the leaflet in a space between the two elements as schematically shown in FIG. 3 and FIG. 4.

It will be appreciated that, as a consequence of this action, the length of the free edge 30 of the leaflet 28 is effectively shortened because the leaflet becomes wrapped around the cylinder, and is held in position. This shortening of the free edge by transcatheter procedure means allows the valve to operate with greater coaptation with an opposing leaflet, and thus with renewed efficiency yet eliminates invasive opening of the heart using conventional open heart techniques.

Figure 5:
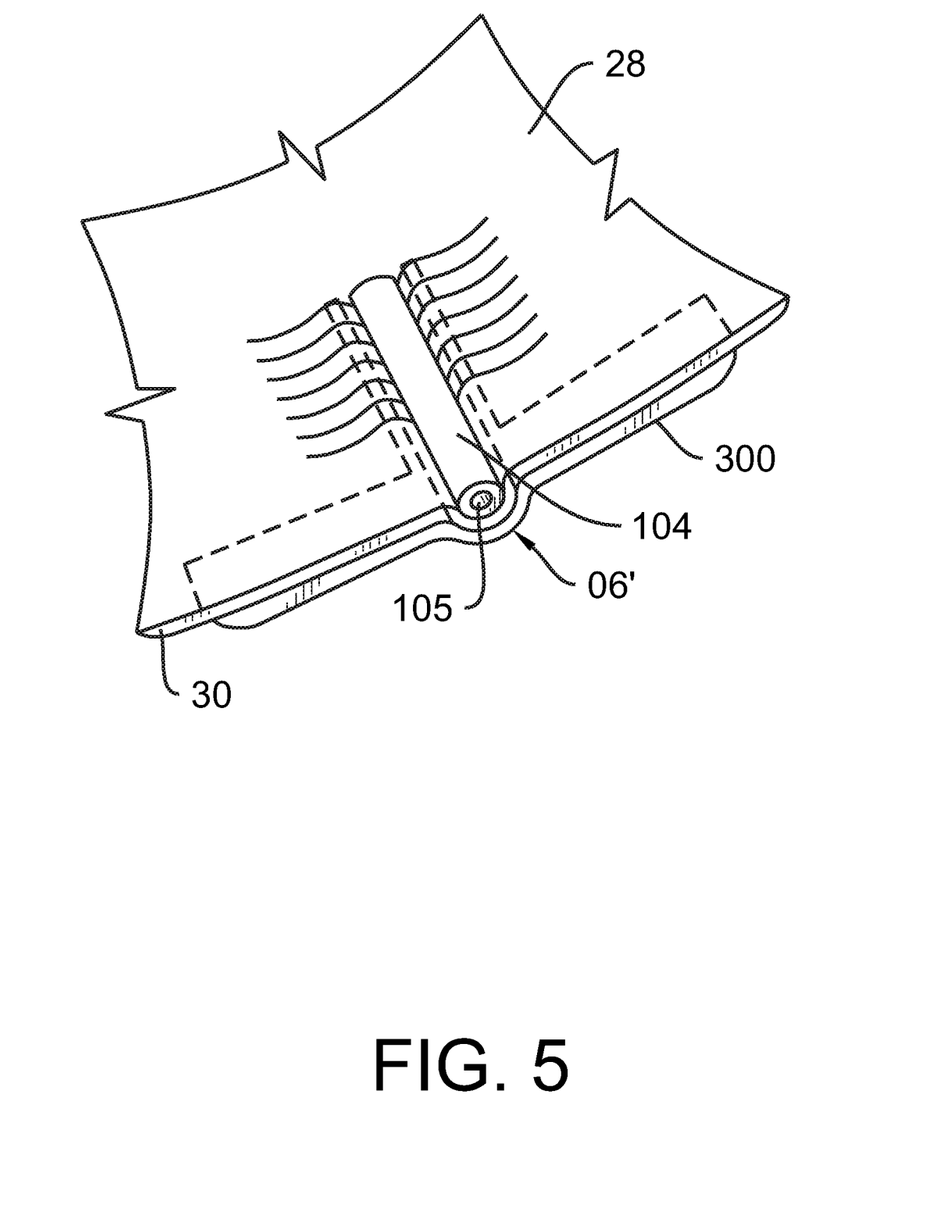
FIG. 5 is a schematic perspective view of a valve leaflet of a human heart onto which another embodiment of a system with magnetic properties has been attached.
Figure 6:
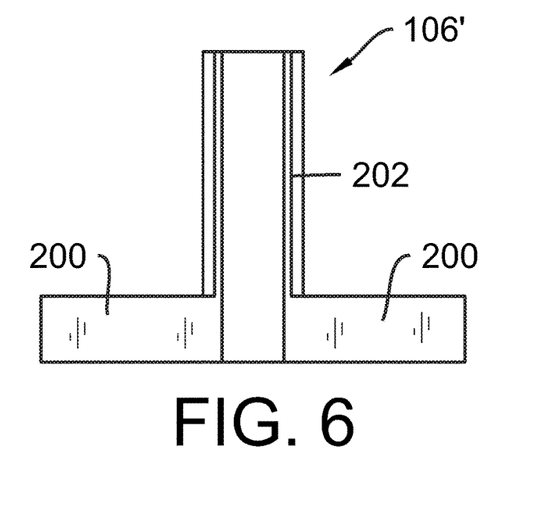
FIG. 6 is a front elevational view of a component of the system with magnetic properties shown in FIG. 5.
Figure 7:
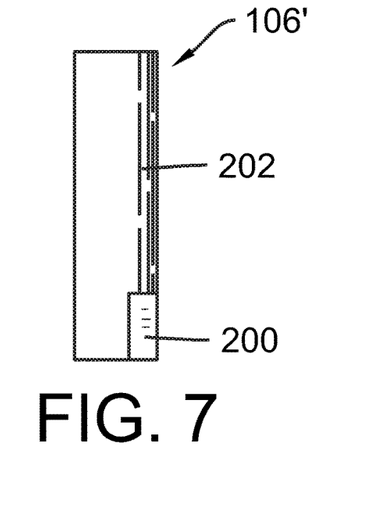
FIG. 7 is a side elevational view of the component shown in FIG. 6.
Figure 8:
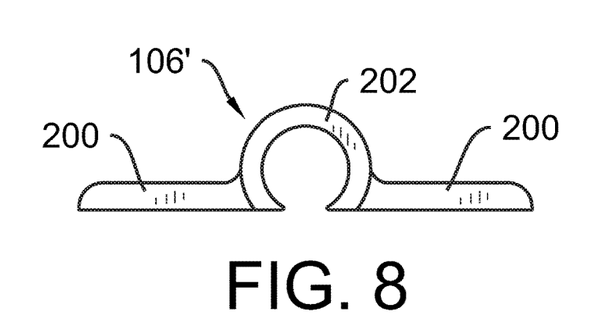
FIG. 8 is a top view of the component shown in FIG. 6.
Figure 9:
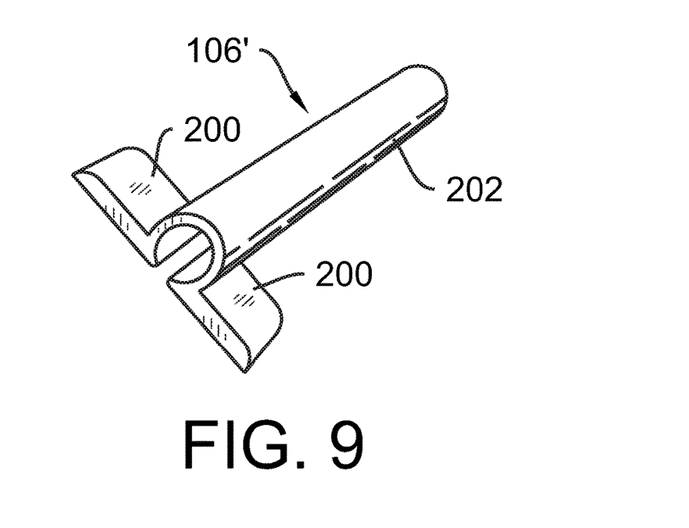
FIG. 9 is a perspective view of the component shown in FIG. 6.

Turning now to a further embodiment of the foregoing, a variation is described with reference to FIGS. 5-9 that provides further advantages under certain conditions. This embodiment is also described in application Ser. No. 15/445,789. Here, a clip 106' is provided, and is modified to include a set of two flanges 200. The flanges are attached to the clip 106' so that they extend perpendicular to a cylindrical portion 202 of the clip. Two flat surfaces on opposite sides of each flange bound the flange. Thus, when the clip 106' of this embodiment is attached to the cylinder 104 to capture a valve leaflet according to the method described above (with modifications that are set forth here) and as seen in FIG. 5, the flanges 200 extend along the surface of the free edge 30 of the leaflet 28 and support it against bending. This has the advantage that when the leaflet is moved toward an opposing leaflet by blood flow, the leaflet does not tend to buckle at the location of the cylinder, and coaptation with the opposing leaflet is strongly enhanced.

Figure 10:
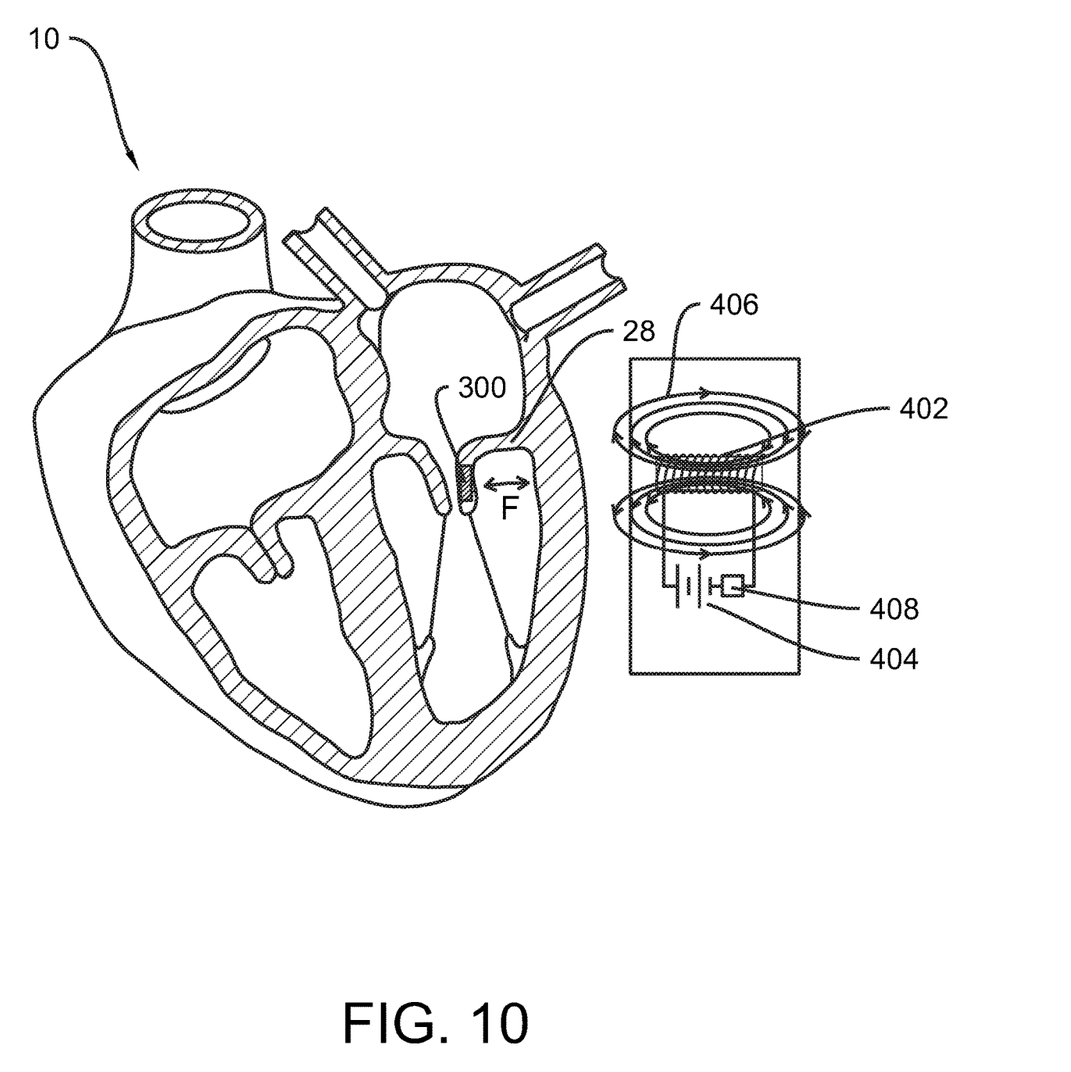
FIG. 10 sectional view of a human heart, showing that the system of FIG. 3 of or FIG. 9 has been attached to a valve leaflet, in conjunction with an electromagnetic field generator adjacent the heart.
Figure 11:
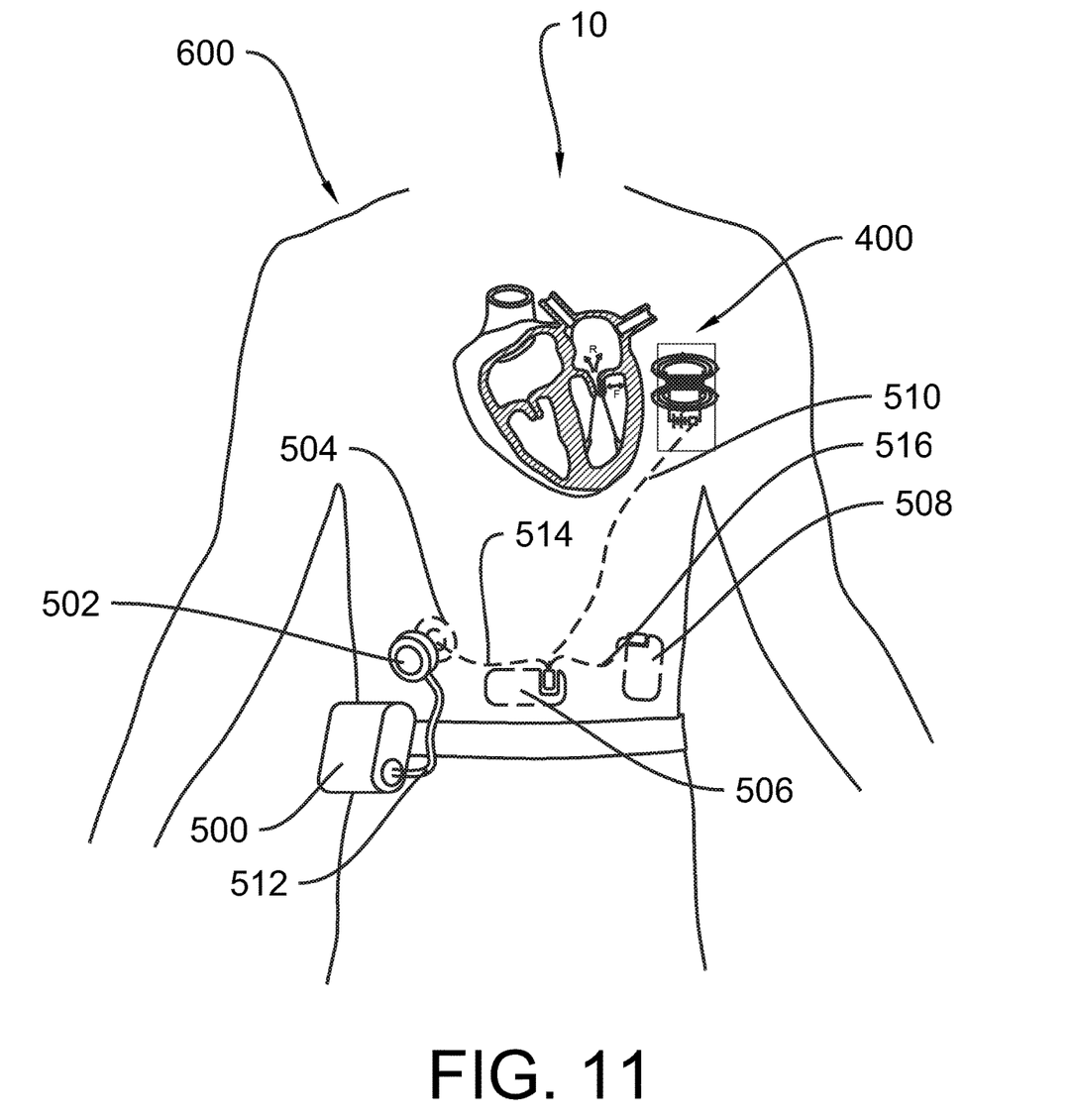
FIG. 11 is a schematic view of a human torso, into which the system of FIG. 10 and electromagnetic field generator has been implanted, together with further operational components.

Turning now to FIGS. 10 and 11, the next aspect of the invention is described. FIG. 10 exemplifies how one of the exemplary structures described above (FIG. 3 or FIG. 5) may be attached to a leaflet 28 of the valve in a patient's heart. Whichever structure is used, it is identified by the numeral 300 in FIG. 10 and referred to herein as the responsive element.

In addition to the responsive element 300, an activation element 400 may be placed within the patient's torso 600 but outside the heart 10 using a minimally invasive technique by known means, via insertion between ribs of the ribcage. The activation element 400 may be positioned between the left lung and the left external wall of the heart, as close to the heart as is feasible.

The activation element 400 comprises the following structures. A cylindrical coil 402 of metallic wire is provided, the ends of which are attached by circuit to a battery 404 for providing electric power. As will be appreciated, this arrangement is sufficient to establish a magnetic field 406 that extends through the coil. The responsive element 300 is fabricated to include a material that is susceptible to a magnetic field and preferably, is formed from a rare earth metal with magnetic properties. The battery and coil are configured so that the magnetic field 406 will extend into the heart 10 and reach the responsive element 300, where it will be strong enough to effect movement thereof. In the circuit between the battery 404 and the coil 402 may be placed a microprocessor 408 for controlling the magnetic field 406 as will be described further below. Significantly, the microprocessor 408 includes electrode sensors according to known technology (not separately shown in the drawings) for determining the natural pulse rate of the heart, and to distinguish between the systolic phase and the diastolic phase of the heart. This information will be used during operation of the system as described below.

Referring now to FIG. 11, additional structure may be provided to enable the system for long term use. An external battery pack 500 may be provided, attached for example to outer clothing of the patient, such as to a belt. An implanted internal rechargeable battery 508 may be implanted under the skin of the patient, according to known methodology. (The rechargeable battery may effectively replace the battery 404 shown in FIG. 10, or supplement it.) The external battery 500 is configured to charge the internal rechargeable battery 508, again according to known methodology, by a wireless energy transfer system which is provided in the following manner. An external energy transmitter 502 (in circuit 512 communication with the external battery 500) is located near the external surface of the patient's skin, while an internal energy receiver 504 is implanted under the skin of the patient at a location to match the location of the energy transmitter 502. The transmission and reception of energy between transmitter 502 and receiver 504 is accomplished by known technology which simply amounts to a transmitting electromagnetic inductive coil located in the transmitter, and a receiving electromagnetic inductive coil located in the receiver. Movement of a magnetic field in the transmitting coil causes a current to flow in the receiving coil via the known process of electromagnetic induction, and this current is passed via implanted circuit wires 514, 516 to the implanted rechargeable battery 508 which, in turn, becomes recharged over time by known technology. The process of recharging the battery 508 is regulated by an implanted internal controller unit 506 according to known technology.

With this structure in place, we turn to the operation of the system. As already described, the responsive element 300 may, on its own, introduce an improved performance of the valve by shortening the length of the free edge 30 of one of the valve leaflets. However, this performance may be further enhanced by the operation of the coil 402 and its magnetic field 406 in the following manner.

The microprocessor 408 in the activation element 400 performs a function that includes monitoring the heartbeat of the patient. The microprocessor is configured to transmit the heart beat information to a switching system, also in the microprocessor, that sends electric current from the rechargeable battery 508 into the coil 402 in a switched sequence. The switching system is programmed to transmit current, first in one direction and then in the opposite direction, so that the polarity of the magnetic field 406 is repeatedly reversed, synchronous with the heartbeat. The switching system is programmed so that, when the heart goes into systole, the magnetic field 406 is set to force the responsive element 300 into a mode that tends to close the leaflets of the valve. This may be a repulsive mode, or an attractive mode, depending on the leaflet to which the responsive element 300 has been attached. Then, as the heart goes into diastole, the magnetic field 402 reverses direction and places the responsive element 300 into a mode that separates and opens the leaflets of the valve. The period of oscillation of the magnetic field 406 is set to match the heartbeat of the patient.

It will be appreciated that this configuration of structure and motion adds greater enhancement and additional advantage to the operation of the leaflets of the valve. The valve itself may operate without the alternating magnetic field 406, which may be turned off by the patient depending on his physical condition. But should there be a sensation of regurgitation after implantation of the responsive element 300, then the patient himself may switch on the current to the electric field to enhance the coaptation of the leaflets and reduce any regurgitation. Alternatively, the system may be set so that the alternating magnetic field 406 cannot be turned off by the patient, but remains in permanent operation or until a service personnel adjusts the programmable contents of the internal controller unit.

Accordingly, there is described a novel and advantageous system that address needs in the art for improving the coaptation between opposing leaflets in a heart valve. The invention requires no open heart surgery, but permits a small magnetically susceptible element to be introduced by transcatheter procedure and attached to a leaflet of the valve. An electromagnet is implanted in the torso of the patient outside of the heart, there is no open heart surgery required, and this procedure too may be minimally invasive. Repeated charging of the energy supply for the system may be accomplished without surgery or a stoma prepared in the skin of the patient. The present invention may, of course, be carried out in other specific ways than those herein set forth without departing from the essential characteristics of the invention. The present embodiments are, therefore, to be considered in all respects as illustrative and not restrictive, while the scope of the invention is set forth in the claims that follow.

We claim:

1. A method for improving the function of a valve in the heart of a patient, comprising:
attaching, to a leaflet of the valve, an element that is responsive to a magnetic field;
positioning, outside of the heart of the patient, a coil connected to a source of electric energy;
activating the source of electric energy to provide an oscillating current in the coil; and thereby
providing an oscillating magnetic field through the coil to effect movement of the element and the leaflet.

2. The method of claim 1, wherein attaching the element includes attaching the element by transcatheter procedure.

3. The method of claim 1, wherein attaching the element includes attaching the element that includes a rare earth metal.

4. The method of claim 1, wherein attaching the element includes shortening a free edge of the leaflet.

5. The method of claim 1, wherein attaching the element comprises:
positioning, above a leaflet of the valve, a first cylinder of the element;
positioning, below the leaflet, a clip of the element having an axial length and comprising a second cylinder having a wall and an internal bore, wherein the wall defines an opening extending along the axial length; and
pressing the first cylinder radially toward the second cylinder and through the opening into the internal bore, and simultaneously forcing a portion of the leaflet into the internal bore between the first cylinder and the second cylinder.

6. The method of claim 5, wherein pressing the first cylinder through the opening into the internal bore includes elastically bending the second cylinder to temporarily widen the opening.

7. The method of claim 6, wherein positioning the first cylinder and positioning the clip are performed using a transcatheter procedure.

8. The method of claim 7, further including positioning an elongate element to extend along a free edge of the leaflet.

9. The method of claim 1, wherein positioning, outside of the heart of the patient, the coil connected to the source of electric energy includes implanting the coil inside a torso of the patient.

10. The method of claim 9, wherein implanting the coil includes implanting the coil between a wall of the heart and a left lung.

11. The method of claim 9, wherein implanting the coil includes implanting the source of electric energy inside a torso of the patient.

12. The method of claim 11, further comprising:
recharging the source of electric energy from a second source of electric energy located outside the torso by a process of electromagnetic induction.

13. The method of claim 1, wherein providing the oscillating magnetic field includes measuring a first frequency of a heart rate of the patient and then synchronizing a second frequency of the oscillating magnetic field with the first frequency.

14. The method of claim 13, wherein synchronizing the second frequency with the first frequency includes forcing the leaflet into coaptation with an opposing leaflet during a systole of the heart, and forcing the leaflet out of coaptation during a diastole of the heart.

* * * * *